US010398662B1

(12) United States Patent
Allphin et al.

(10) Patent No.: US 10,398,662 B1
(45) Date of Patent: Sep. 3, 2019

(54) GHB FORMULATION AND METHOD FOR ITS MANUFACTURE

(71) Applicant: JAZZ PHARMA IRELAND LIMITED, Dublin (IE)

(72) Inventors: Clark Allphin, Seattle, WA (US); Scott Bura, Gilroy, CA (US)

(73) Assignee: JAZZ PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 15/047,586

(22) Filed: Feb. 18, 2016

Related U.S. Application Data

(60) Provisional application No. 62/117,889, filed on Feb. 18, 2015.

(51) Int. Cl.
*A61K 31/19* (2006.01)
*A61K 31/785* (2006.01)
*A61K 9/50* (2006.01)
*A61K 38/02* (2006.01)

(52) U.S. Cl.
CPC ............ *A61K 31/19* (2013.01); *A61K 9/5031* (2013.01); *A61K 31/785* (2013.01); *A61K 38/02* (2013.01)

(58) Field of Classification Search
CPC ...... A61K 35/00; A61K 31/19; A61K 31/785; A61K 38/02; A61K 9/5031
USPC .................................................. 424/494, 187
See application file for complete search history.

(56) References Cited

U.S. PATENT DOCUMENTS

| 3,051,619 | A | 8/1962 | Laborit |
| 3,419,588 | A | 12/1968 | De Man |
| 4,221,778 | A | 9/1980 | Raghunathan |
| 4,374,441 | A | 2/1983 | Carter et al. |
| 4,393,236 | A | 7/1983 | Klosa |
| 4,510,128 | A | 4/1985 | Khanna |
| 4,687,662 | A | 8/1987 | Schobel |
| 4,738,985 | A | 4/1988 | Kluger et al. |
| 4,916,161 | A | 4/1990 | Patell |
| 4,939,949 | A | 7/1990 | Langenberg |
| 4,983,632 | A | 1/1991 | Gessa et al. |
| 5,294,430 | A | 3/1994 | Borch et al. |
| 5,380,937 | A | 1/1995 | Koehler et al. |
| 5,415,870 | A | 5/1995 | Gergely et al. |
| 5,594,030 | A | 1/1997 | Conte et al. |
| 5,753,708 | A | 5/1998 | Koehler et al. |
| 5,840,331 | A | 11/1998 | Van Cauter et al. |
| 5,955,106 | A | 9/1999 | Moeckel et al. |
| 5,990,162 | A | 11/1999 | Scharf |
| 6,022,562 | A | 2/2000 | Autant et al. |
| 6,322,819 | B1 | 11/2001 | Burnside et al. |
| 6,384,020 | B1 | 5/2002 | Flanner et al. |
| 6,436,998 | B1 | 8/2002 | Cacciaglia et al. |
| 6,472,431 | B2 | 10/2002 | Cook et al. |
| 6,472,432 | B1 | 10/2002 | Perricone |
| 6,780,889 | B2 | 8/2004 | Cook et al. |
| 7,262,219 | B2 | 8/2007 | Cook et al. |
| 7,568,822 | B2 | 8/2009 | Ibrahim |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,851,506 | B2 | 12/2010 | Cook et al. |
| 7,895,059 | B2 | 2/2011 | Reardan et al. |
| 8,101,209 | B2 | 1/2012 | Legrand et al. |
| 8,193,211 | B2 | 6/2012 | Liang et al. |
| 8,202,537 | B2 | 6/2012 | Mehta et al. |
| 8,263,650 | B2 | 9/2012 | Cook et al. |
| 8,324,275 | B2 | 12/2012 | Cook et al. |
| 8,461,197 | B2 | 6/2013 | Tung |
| 8,461,203 | B2 | 6/2013 | Cook et al. |
| 8,529,954 | B2 | 9/2013 | Lebon et al. |
| 8,591,922 | B1 | 11/2013 | Allphin et al. |
| 8,598,191 | B2 | 12/2013 | Liang et al. |
| 8,680,228 | B2 | 3/2014 | Guo et al. |
| 8,731,963 | B1 | 5/2014 | Reardan et al. |
| 8,759,394 | B2 | 6/2014 | Tung et al. |
| 8,771,735 | B2 | 7/2014 | Rourke et al. |
| 8,772,306 | B1 | 7/2014 | Eller |
| 8,778,301 | B2 | 7/2014 | Mamelak et al. |
| 8,778,398 | B2 | 7/2014 | Rourke et al. |
| 8,859,619 | B2 | 10/2014 | Cook et al. |
| 8,901,173 | B2 | 12/2014 | Allphin et al. |
| 9,770,514 | B2 | 9/2017 | Ghebre-Sellassie |
| 2003/0180249 | A1* | 9/2003 | Khanna ............ A61K 47/48184 424/78.1 |
| 2004/0092455 | A1 | 5/2004 | Mamelak et al. |
| 2005/0031688 | A1 | 2/2005 | Ayala |
| 2005/0037077 | A1 | 2/2005 | Legrand et al. |
| 2005/0142192 | A1 | 6/2005 | Benjamin et al. |
| 2006/0018933 | A1 | 1/2006 | Vaya et al. |
| 2006/0024365 | A1 | 2/2006 | Vaya et al. |
| 2006/0069040 | A1 | 3/2006 | Mamelak |
| 2006/0210630 | A1 | 9/2006 | Liang et al. |
| 2007/0270491 | A1 | 11/2007 | Cook et al. |
| 2008/0003267 | A1 | 1/2008 | Spencer et al. |
| 2008/0069871 | A1 | 3/2008 | Vaughn et al. |
| 2008/0118571 | A1 | 5/2008 | Lee et al. |
| 2008/0226564 | A1 | 9/2008 | Weers et al. |
| 2008/0292700 | A1 | 11/2008 | Nghiem et al. |
| 2008/0293698 | A1 | 11/2008 | Johnson |
| 2009/0137565 | A1 | 5/2009 | Frucht |
| 2010/0112056 | A1 | 5/2010 | Rourke et al. |
| 2011/0039929 | A1 | 2/2011 | Cook et al. |
| 2011/0111027 | A1 | 5/2011 | Rourke et al. |
| 2012/0020833 | A1 | 1/2012 | Cook et al. |
| 2012/0076865 | A1* | 3/2012 | Allphin ................ A61K 9/2054 424/495 |

(Continued)

FOREIGN PATENT DOCUMENTS

CA 2 112 663 C 4/2002
CN 102905688 A 1/2013

(Continued)

OTHER PUBLICATIONS

Borgen et al; title: The influence of gender and food on the pharmacokinetics of sodium oxybate oral solution in healthy subjects; J Clin Pharmacol. Jan. 2003;43(1):59-65.*

(Continued)

*Primary Examiner* — Yanzhi Zhang
(74) *Attorney, Agent, or Firm* — Cooley LLP

(57) ABSTRACT

The present application relates to GHB formulations and methods for manufacturing the same.

21 Claims, No Drawings

(56) References Cited

U.S. PATENT DOCUMENTS

| | | | |
|---|---|---|---|
| 2012/0148672 | A1 | 6/2012 | Mehta et al. |
| 2012/0202879 | A1 | 8/2012 | Cook et al. |
| 2012/0202880 | A1 | 8/2012 | Cook et al. |
| 2013/0273159 | A1 | 10/2013 | Howard et al. |
| 2014/0004202 | A1 | 1/2014 | Suplie et al. |
| 2014/0037745 | A1 | 2/2014 | Liang et al. |
| 2014/0093578 | A1 | 4/2014 | Mehta et al. |
| 2014/0127306 | A1 | 5/2014 | Mehta et al. |
| 2014/0348917 | A1 | 11/2014 | Rourke et al. |
| 2015/0073052 | A1 | 3/2015 | Cook et al. |
| 2016/0068463 | A1 | 3/2016 | Peoples et al. |
| 2016/0228379 | A1 | 8/2016 | Kumar et al. |
| 2016/0271070 | A1 | 9/2016 | Singh et al. |
| 2016/0346200 | A1 | 12/2016 | Sommer et al. |
| 2016/0346216 | A1 | 12/2016 | Chen |
| 2017/0119627 | A1 | 5/2017 | Bhargava et al. |
| 2017/0340519 | A9 | 11/2017 | Bhargava et al. |
| 2018/0008539 | A1 | 1/2018 | Singh et al. |
| 2018/0021284 | A1 | 1/2018 | Mégret et al. |
| 2018/0318222 | A1 | 11/2018 | Allphin et al. |

FOREIGN PATENT DOCUMENTS

| | | | |
|---|---|---|---|
| CN | 102958930 A | 3/2013 | |
| CN | 103209966 A | 7/2013 | |
| CN | 103209967 A | 7/2013 | |
| EP | 0203768 A2 | 12/1986 | |
| EP | 0235408 A1 | 9/1987 | |
| EP | 0344704 A1 | 12/1989 | |
| EP | 0616804 A1 | 9/1994 | |
| EP | 0635265 A1 | 1/1995 | |
| EP | 0709087 B1 | 12/1999 | |
| EP | 0635265 B1 | 2/2000 | |
| EP | 1140061 A2 | 10/2001 | |
| EP | 1140061 B1 | 5/2003 | |
| EP | 1316309 A1 | 6/2003 | |
| EP | 2760911 B1 | 11/2017 | |
| EP | 1434572 B1 | 12/2017 | |
| GB | 922029 A | 3/1963 | |
| JP | S57042651 A | 3/1982 | |
| JP | 62-12715 A | 1/1987 | |
| JP | 04049212 A | 2/1992 | |
| JP | 05508422 A | 11/1993 | |
| JP | H06-508839 A | 10/1994 | |
| JP | 7-53365 A | 2/1995 | |
| JP | H8-511257 A | 11/1996 | |
| JP | 09-104620 A | 4/1997 | |
| JP | H10-505604 A | 6/1998 | |
| JP | 2001513552 A | 9/2001 | |
| JP | 2004-514732 A | 5/2004 | |
| JP | 2007-521231 A | 8/2007 | |
| JP | 2008512386 A | 4/2008 | |
| JP | 2008519847 A | 6/2008 | |
| JP | 2008-528571 A | 7/2008 | |
| JP | 2009-532331 A | 9/2009 | |
| JP | 2011-500865 A | 1/2011 | |
| RU | 2210360 C1 | 8/2003 | |
| WO | WO 1994/028880 A1 | 12/1994 | |
| WO | WO 1996/040105 A1 | 12/1996 | |
| WO | WO 1999/009972 A1 | 3/1999 | |
| WO | WO 2000/038672 A2 | 7/2000 | |
| WO | WO 2002/045684 A2 | 6/2002 | |
| WO | WO 2005/016318 A1 | 2/2005 | |
| WO | WO 2005/099671 A2 | 10/2005 | |
| WO | WO 2006/029155 A2 | 3/2006 | |
| WO | WO 2006/053186 A2 | 5/2006 | |
| WO | WO 2006/080029 A1 | 8/2006 | |
| WO | WO 2007/103200 A2 | 9/2007 | |
| WO | WO 2009/056550 A2 | 5/2009 | |
| WO | WO 2010/053691 A1 | 5/2010 | |
| WO | WO 2010/055260 A1 | 5/2010 | |
| WO | WO 2011/119839 A1 | 9/2011 | |
| WO | WO 2011/127252 A2 | 10/2011 | |
| WO | WO 2011/135461 A2 | 11/2011 | |
| WO | WO 2011/139271 A1 | 11/2011 | |
| WO | WO 2011/140310 A2 | 11/2011 | |
| WO | WO 2012/028688 A1 | 3/2012 | |
| WO | WO 2012/107652 A1 | 8/2012 | |
| WO | WO 2014/078014 A2 | 5/2014 | |
| WO | WO 2015/120006 A1 | 8/2015 | |
| WO | WO 2015/120110 A2 | 8/2015 | |
| WO | WO 2016/087952 A1 | 6/2016 | |
| WO | WO 2016/178132 A1 | 10/2016 | |
| WO | WO 2015/166473 A1 | 3/2017 | |
| WO | WO 2017/182851 A1 | 10/2017 | |
| WO | WO 2018/015563 A1 | 1/2018 | |

OTHER PUBLICATIONS

Unknown author, titel: definition of biotransformation;Medical dictionary; downloaded from https://medical-dictionary.thefreedictionary.com/biotransformation on Jun. 21, 2018. (Year: 2018)*

Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.

Anand et al. "Ion-exchange resins: carrying drug delivery forward." Drug Discovery Today (2001); 6.17: 905-914.

Caballero et al. "Characterization of alginate beads loaded with ibuprofen lysine salt and optimization of the preparation method." International Journal of Pharmaceutics (2014); 460.1: 181-188.

Davis et al. "Active chloride secretion in the normal human jejunum." J Clin Invest. (1980); 66(6): 1326-1333.

Mahore et al. "Ion exchange resins: pharmaceutical applications and recent advancement." Int J Pharm Sci Rev Res (2010); 1.2: 8-13.

Munot et al. "Ion exchange resins in pharmaceuticals: A review." Journal of Pharmacy Research (2010); 3(12): 2928-2929.

Ohta et al. "Development of a simple method for the preparation of a silica gel based controlled delivery system with a high drug content." European Journal of Pharmaceutical Sciences (2005); 26.1: 87-96.

Patil et al. "A review on ionotropic gelation method: novel approach for controlled gastroretentive gelispheres." International Journal of Pharmacy and Pharmaceutical Sciences (2012); 4.4: 27-32.

Puguan et al. "Diffusion characteristics of different molecular weight solutes in Ca-alginate gel beads." Colloids and Surfaces A: Physicochemical and Engineering Aspects (2015); 469: 158-165.

Rohm and Haas. "Duolite AP143/1083 Pharmaceutical Grade Anion Exchange Resin." Feb. 2006, 4 pages.

Seno and Yamabe. "The Rheological Behavior of Suspensions of Ion-exchange Resin Particles." Bulletin of the Chemical Society of Japan (1966); 39.4: 776-778.

Singh et al. "Ion exchange resins: drug delivery and therapeutic applications." Fabad J. Pharm. Sci (2007); 32: 91-100.

Srikanth et al., "Ion-exchange resins as controlled drug delivery carriers." Journal of Scientific Research (2010); 2.3: 597-611.

Takka and Gürel. "Evaluation of chitosan/alginate beads using experimental design: formulation and in vitro characterization." AAPS PharmSciTech (2010); 11.1: 460-466.

The Dow Chemical Company, Product Data Sheet for AMBERLITE™ IRN78 Resin. Form No. 177-02230-0311, Rev. 0, 3 pages.

Turnberg, L.A. "Abnormalities in intestinal electrolyte transport in congenital chloridorrhoea." Gut. (1971); 12(7): 544-551.

Broughton, et al. "Effects of Nocturnal Gamma-Hydroxybutyrate on Spell/Waking Patterns in Narcolepsy-Cataplexy." Can J. Neural Sci (1980); 7 (1): 23-31.

Ferrara, S. D., et al., "Pharmacokinetics of Y-Hydroxybutyric Acid in Alcohol Dependent Patients After Single and Repeated Oral Doses." Br. J. Clin. Pharmacol. (1992); 34: 231-235.

Frucht, S.J., et al., "A Single-Blind, Open-Label Trial of Sodium Oxybate for Myoclonus and Essential Tremor," Neurology (2005); 65 (12): 1967-1970.

Grove-White, I. G., "Critical Flicker Frequency after Small Doses of Methohexitone, Diazepam and Sodium 4-Hydroxybutyrate." Brit. J. Anaesth (1971); 43 (2): 110-112.

Grove-White, I. G., et al., "Effect of Methohexitone, Diazepam and Sodium 4-Hydroxybutyrate on Short-Term Memory." Brit. J. Anaesth (1971); 43 (2): 113-116.

(56) References Cited

OTHER PUBLICATIONS

Hasenbos, M.A., et al., "Anaesthesia for bullectomy. A technique with spontaneous ventilation and extradural blockade." Anaesthesia (1985); 40 (10): 977-980.
Lammers, G. J., "Gammahydroxybutyrate and Narcolepsy: A Double-Blind Placebo-Controlled Study." Sleep (1993); 16 (3): 216-220.
Lapierre, O., "The Effect of Gamma-Hydroxybutyrate on Nocturnal and Diurnal Sleep of Normal Subjects: Further Considerations on REM Sleep-Triggering Mechanisms." Sleep (1990); 13 (1): 24-30.
Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with γ-hydroxybutyrate. A review of Clinical and Sleep Laboratory Findings." Sleep (1986); 9 (1): 285-290.
Neuman, Ariel, "GHB's Path to Legitimacy: An Administrative and Legislative History of Xyrem." Apr. 2004, Harvard Law School, Class of 2005, Food and Drug Law, Winter Term 2004, Professor Peter Barton Hutt. (2004), 1-39.
Ondo, William G., et al., "Sodium Oxybate for Excessive Daytime Sleepiness in Parkinson's Disease: A Polysomnographic Study." Arch. Neural. (2008); 65 (10): 1337-1340.
Palatini, P., "Dose Dependent Absorption and Elimination of Gamma-Hydroxybutyric Acid in Healthy Volunteers." Eur. J. Clin. Pharmacol. (1993); 45 (4): 353-356.
Russel, I. Jon, et al., "Sodium Oxybate Relieves Pain and Improves Function in Fibromyalgia Syndrome." Arthritis. Rheum. (2009); 60 (1): 299-309.
Scrima, L., "The Effects of γ-Hydroxybutyrate on the Sleep of Narcolepsy Patients: A Double-Blind Study." Sleep (1990); 13 (6): 479-490.
Suner, Selim, et al., "Pediatric Gamma Hydroxybutyrate Intoxication." Acad Emerg. Med. (1997); 4 (11): 1041-1045.
"HIB-IMUNE," Physicians Desk Reference (41st ed.), (1987), 1095-1096.
"HibVAX,", Physicians Desk Reference (41st ed.), (1987), 870.
"Matic Acid," The Handbook of Pharmaceutical Excipients, 2nd Ed., (1994 ), pp. 285-286, 633.
"Phospholine Iodide," Physicians Desk Reference (50th ed.), (1996), 2784.
"Taxotere," Physicians Desk Reference (51st ed.), (1997), 2204-2207.
21 C.F.R. 184, Food and Drug Administration, HHS, (1998), pp. 441-535.
Activase, Physicians Desk Reference (50th ed.), (1996), pp. 312, 1058-1061.
Bedard, "Nocturnal γ-Hydroxybutyrate—Effect on Periodic Leg Movements and Sleep Organization of Narcoleptic Patients," Clin Neuropharmacol., 12(1), Feb. 1989, 29-36.
Berner, Jon E., "A Case of Sodium Oxybate Treatment of Tardive Dyskinesia and Bipolar Disorder," J. Clin. Psychiatry, 2008, 69:5, p. 862.
Berthier, et al., "Possible Involvement of a Gamma-Hydroxybutyric Acid Receptor in Startle Disease," Acta Paediatr, 83, 1994, 678-680.
Borgen, L., et al. "Xyrem® (sodium oxybate): A Study of Dose Proportionality in Healthy Human Subjects." J. Clin. Pharmacol. (2000); 40: 1053.
Broughton et al., "The Treatment of Narcolepsy-Cataplexy with Nocturnal Gamma-Hydroxybutyrate." Can J. Neural Sci (1979); 6(1): 1-6.
Broughton, et al. "Gamma-Hydroxy-Butyrate in the Treatment of Narcolepsy: a Preliminary Report." (1976) Narcolepsy, Ny, N.Y., Spectrum Publications, Inc. 659-668.
Chem Abstract ES302338, SciFinder®, (1964), 1 pg.
Chemical Abstracts: Seventh Collective Index, vols. 56-65, (1962-1966), 4 pgs.
Ferris, T.J., et al., "Synthesis, characterisation and detection of gamma-hydroxybutyrate salts," Forensic Science International, 2012, 216: 158-162.

Frucht, et al. "A Pilot Tolerability and Efficacy Trial of Sodium Oxybate in Ethanol-Responsive Movement Disorders." Movement Disorders (2005); 20 (10): 1330-1337.
Gallimberti, L., "Gamma-hydroxybutyric Acid for Treatment of Alcohol Withdrawal Syndrome," The Lancet, 2(8666), (1989), 787-789.
Gallimberti, L., "Gamma-Hydroxybutyric Acid in the Treatment of Alcohol Dependence: A Double-Blind Study," Alcohol Clin. Exp. Res. (1992), 16(4): 673-676.
Gerra, G., et al., "Flumazenil effects on growth hormone response to gamma-hydroxybutyric acid," Int Clin Psychopharmacol. (1994); 9 (3): 211-215.
Gessa, G. L., "Gamma-hydroxybutyric Acid in the Treatment of Alcohol Dependence," Clin. Neuropharm., vol. 15 Suppl 1 Pt A, (1992), 303a-304a.
Gessa, G. L., et al., "Gamma-hydroxybutyric acid (GHB) for treatment of ethanol dependence," European Neuropsychopharmacology, 3(3), (1993), 224-225.
Hoes, M. J., "Gamma-hydroxybutyric acid (*) as hypnotic. Clinical and pharmacokinetic evaluation of gamma-hydroxybutyric acid as hypnotic in man," L'Encéphale: Revue de psychiatrie clinique biologique et thérapeutique (1980); 6 (1): 93-99.
Laborit, H., "Gamma-Hydroxybutyrate, Succinic Semialdehyde and Sleep," Laboratoire d'Eutonologie, (1973), 257-274.
Ladinsky, H., et al., Mode of Action of Gamma-Butyrolactone on the Central Cholinergic System, Naunyn-Schmiedeberg's Arch. Pharmacol. (1983); 322 (1): 42-48.
Lapierre et al., "The Effect of Gamma-Hydroxybutyrate: A Double-Blind Study of Normal Subjects," Sleep Research (1988); 17, 1988, 6 pages. (Abstract Only).
Lee, C. R., "Evidence for the β-oxidation of orally administered 4-hydroxybutyrate in humans." Biochemical Medicine (1977); 17 (3): 284-291.
Lubrano, et al. "Fibromyalgia in Patients with Irritable Bowel Syndrome. An Association with the Severity of the Intestinal Disorder." Int J Colorectal Dis. (2001); 16 (4): 211-215.
Mamelak, et al. The Effects of γ-Hydroxybutyrate on Sleep. Biol Psych (1977); 12 (2): 273-288.
Mamelak, M., "Gammahydroxybutyrate: An endogenous regulator of energy metabolism." Neuroscience and Biobehavioral Reviews (1989); 13 (4): 187-198.
Mamelak, M., "Sleep-Inducing Effects of Gammahydroxybutyrate." The Lancet (1973); 302 (7824): 328-329.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.
Morrison, Robert Thornton, et al., Organic Chemistry, 3rd Edition, (1973), pp. 672-677.
Nema, S, et al., "Excipients and Their Use in Injectable Products." PDA J. Pharm. Sci. Technol. (1997); 51(4): 166-171.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES), (Sep. 14, 2012).
Outlaw, et al. "Dyspepsia and its Overlap with Irritable Bowel Syndrome." Curr Gastroenterol Rep. (2006); 8 (4): 266-272.
Remington. The Science and Practice of Pharmacy. 20th Edition, Gennaro, Ed,. Lippincott Williams & Wilkins (2000). (See e.g. p. 861).
Remington. The Science and Practice of Pharmacy. 20th Edition, Gennaro, Ed,. Lippincott Williams & Wilkins. Chapter 45 (Oral Solid Dosage Forms) (2000).
Roth, et al., "γ-Butyrolactone and γ-Hydroxybutyric Acid-I, Distribution and Metabolism." Biochemical Pharmacology (1966); 15 (9):1333-1348.
Roth, R. H., et al., "γ-Butyrolactone and γ-Hydroxybutyric acid-II. The Pharmacologically active form." J. Neuropharmacol. (1966); 5 (6): 421-428.
Roxane Laboratories, Inc.'s Answer and Affirmative Defenses to Plaintiff's Complaint, (Jan. 4, 2013).

(56) References Cited

OTHER PUBLICATIONS

Roxane Laboratories, Inc.'s Answer, Affirmative Defenses and Counterclaims to Plaintiff's Complaint, (Dec. 29, 2010).
Roxane Laboratories, Inc.'s Answer, Affirmative Defenses and Counterclaims to Plaintiff's Complaint, (Jun. 1, 2011 ).
Roxane Laboratories, Inc.'s Answer, Affirmative Defenses and Counterclaims to Plaintiff's Complaint, (Mar. 9, 2011 ).
Roxane Laboratories, Inc.'s Answer, Affirmative Defenses and Counterclaims to Plaintiff's Complaint, (Nov. 9, 2012).
Roxane Laboratories, Inc.'s Intitial Invalidity and Noninfringement Contentions Pursuant to Local Patent Rule 3.6, (Apr. 14, 2011 ).
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Scharf, M. B., "The Effects and Effectiveness of γ-Hydroxybutyrate in Patients with Narcolepsy." J. Clin. Psychiatry (1985); 46 (6): 222-225.
Scharf, M. B., et al., "GHB—New Hope for Narcoleptics?" Biol Psychiatry (1989); 26 (4): 329-330.
Scharf, Martin B., et al., "The Effects of Sodium Oxybate on Clinical Symptoms and Sleep Patterns in Patients with Fibromyalgia." J. Rheumatol. (2003); 30 (5): 1070-1074.
Scrima, et al., "Effect of Gamma-Hydroxybutyrate on a Patient with Obstructive Sleep Apnea." Sleep Research (1987); 16: 137.
Scrima, et al., "Effect of High Altitude on a Patient with Obstructive Sleep Apnea." Sleep Research (1987); 16: 427.
Scrima, et al., "Effects of Gamma-Hydroxybutyrate (GHB) on Narcolepsy-Cataplexy Symptoms and MSLT Results in Male and Female Patients." Association of Professional Sleep Societies (1988); 251.
Scrima, et al., "Gamma-Hydroxybutyrate Effects on Cataplexy and Sleep Attacks in Narcoleptics." Sleep Research (1987); 16: 134.
Scrima, L., et al., "Efficacy of Gamma-Hydroxybutyrate Versus Placebo in Treating Narcolepsy-Cataplexy: Double-Blind Subjective Measures," Biol. Psychiatry (1989); 26 (4): 331-343.
Scrima, L., et al., "Narcolepsy." New England J. Med. (1991); 324 (4): 270-272.
Series, F., "Effects of Enhancing Slow-Wave Sleep by Gamma-Hydroxybutyrate on Obstructive Sleep Apnea." Am. Rev. Respir. Dis. (1992); 145 (6): 1378-1383.
Snead, et al., "Ontogeny of y-Hydroxybutyric Acid. I. Regional Concentration in Developing Rat, Monkey and Human Brain." Dev. Brain Res. (1981); 227 (4): 579-589.
Snead, O. Carter, "γ-Hydroxybutyrate Model of Generalized Absence Seizures: Further Characterization and Comparison with Other Absence Models." Epilepsia (1988); 29 (4): 361-368.
Stock, G., "Increase in brain dopamine after axotomy or treatment with Gammahydroxybutyric acid due to elimination of the nerve impulse flow." Naunyn-Schmiedeberg's Arch. Pharmacol. (1973); 278 (4): 347-361.
Strong, A.J., "γ-Hydroxybutyric acid and intracranial pressure." The Lancet (1984); 1 (8389): 1304.
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).
Tunnicliff, Godfrey, "Sites of Action of Gamma-Hydroxybutyrate (GHB)—A Neuroactive Drug with Abuse Potential." Clinical Toxicology (1997); 35 (6): 581-590.
United States Pharmacopeial Convention, Inc.: The National Formulary, 23/NF18, (1995), p. 2205.
Van Den Bogert, A. G., et al., "Placentatransfer of 4-hydroxybutyric acid in man," Anaesthesiology and Intensive Care Medicine (1978); 110: 55-64.
Vickers, M.D., "Gammahydroxybutyric Acid." Int. Anesth. Clinic (1969); 7 (1): 75-89.
Wermuth (Ed.), The Practice of Medicinal Chemistry, Academic Press, Third Edition, "Preparation of Water-Soluble Compounds Through Salt Formulation," Chapter 37, 2008, p. 758, 6 pages.
World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf#page=359.
Yamada, Y., "Effect of Butyrolactone and Gamma-Hydroxybutyrate on the EEG and Sleep Cycle in Man." Electroencephalography and Clinical Neurophysiology (1967); 22 (6): 558-562.
Zheng (Ed.), "Formulation and Analytical Development for Low-Dose Oral Drug Products," John Wiley & Sons, Inc., Hoboken, New Jersey, Table 4.1, p. 65, 2009, 3 pages.

* cited by examiner

GHB FORMULATION AND METHOD FOR ITS MANUFACTURE

CROSS REFERENCE TO RELATED APPLICATION

The present application claims priority to U.S. Provisional Application No. 62/117,889, filed Feb. 18, 2015, the disclosure of which is herein incorporated by reference in its entirety for all purposes.

BACKGROUND OF THE INVENTION

Gamma-hydroxybutyrate (GHB), also known as "oxybate," is an endogenous compound with hypnotic properties that is found in many human body tissues. GHB is present, for example, in the mammalian brain and other tissues. In the brain, the highest GHB concentration is found in the hypothalamus and basal ganglia and GHB is postulated to function as a neurotransmitter (See Snead and Morley, 1981, Brain Res. 227(4): 579-89). The neuropharmacologic effects of GHB include increases in brain acetylcholine, increases in brain dopamine, inhibition of GABA-ketoglutarate transaminase and depression of glucose utilization but not oxygen consumption in the brain. GHB treatment substantially reduces the signs and symptoms of narcolepsy, i.e., daytime sleepiness, cataplexy, sleep paralysis, and hypnagogic hallucinations. In addition, GHB increases total sleep time and REM sleep, and it decreases REM latency, reduces sleep apnea, and improves general anesthesia (see, e.g., U.S. Pat. Nos. 6,472,431; 6,780,889; 7,262,219; 7,851,506; 8,263,650; and 8,324,275; each of which is incorporated herein by reference in its entirety).

Sodium oxybate (Na.GHB), commercially sold as Xyrem®, is approved for the treatment of excessive daytime sleepiness and cataplexy in patients with narcolepsy. It can be used for other sleep time disturbances. Na.GHB has also been reported to be effective for relieving pain and improving function in patients with fibromyalgia syndrome (See Scharf et al., 2003, J. Rheumatol. 30: 1070; Russell et al., 2009, Arthritis. Rheum. 60: 299), and in alleviating excessive daytime sleepiness and fatigue in patients with Parkinson's disease, improving myoclonus and essential tremor, and reducing tardive dyskinesia and bipolar disorder (See Ondo et al., 2008, Arch. Neural. 65: 1337; Frucht et al., 2005, Neurology 65: 1967; Berner, 2008, J. Clin. Psychiatry 69: 862).

SUMMARY OF THE INVENTION

GHB has a short in vivo half-life, so various embodiments of the invention include a formulation and a method for manufacturing a GHB formulation. One embodiment of the invention is a GHB formulation comprising polymeric beads and pharmaceuticals acceptable excipients. The formulation can be a solid or a liquid. Additional agents, such as surfactants, may be added to control the release of GHB from within the polymeric bead, such as sodium lauryl sulfate or stearic acid. The beads can be coated with a flexible film. Optionally, the formulation can contain supplemental anions separate from the coated or uncoated resin particles to facilitate exchange of the GHB when natural (e.g., physiologically produced) anions in the gut are depleted.

In another embodiment of the invention, a precursor to GHB, called gamma butyrolactone (GBL) is loaded onto a hydroxide form Type 1 strong base anion resin (or its equivalent) and the GBL is converted to GHB in the bead to form a GHB resinate product. One can achieve high loading efficiency of the GHB resinate product and a high reaction rate on the resin. Furthermore, organic non-anionic byproducts made in reaction or present in the GBL would not be captured on the resin.

In another embodiment of the invention, one can fully load GHB on the resin, then load a lipophilic agent on the resin with higher selectivity for the resin than GHB. The agent will slow the release of GHB.

In another embodiment, one can fully load an anionic hydrophobic agent, such as stearic acid, onto the resin with lower selectivity for the resin than GHB and then subsequently load GHB less completely, thereby retaining much of the hydrophobic agent and promoting a slower release of GHB.

In still another embodiment of the invention, the hydroxide-bearing resin beads are coated with a flexible film, then loaded with GBL which, in turn, will diffuse through the film and react with the hydroxyl anions of the resin and form the GHB resinate in-situ. The coating will provide further controlled release characteristics. Examples of such coatings include films comprising polyvinyl acetate (PVAcetate), Eudragit RS, ethylcellulose, cellulose acetate or an enteric coating such as acrylic acid-based Eudragit L100, FS100 or L55, cellulose acetate phthalate, and shellac. It is understood that these films can be modified with pore formers to adjust permeability or degree of enteric protection. The coating may also be combined with suitable plasticizer and anti-tack agents to facilitate coating. Finely ground resin beads may also be encapsulated within polysaccharide gel structures that confer enteric protection, through ionotropic gelation as with calcium alginate encapsulation.

Other embodiments include reducing the amount of water in the formulation. Oral administration may be achieved while reducing the amount of water by using agents that increase flow, such as slippants to reduce viscosity. Example slippants include polyethylene oxide (PEG) (and its equivalents) which is available in various grades of varying molecular weight and molecular weight distribution.

DETAILED DESCRIPTION OF THE INVENTION

One embodiment of the invention is a GHB formulation comprising polymeric beads and pharmaceuticals acceptable excipients. The formulation can be in the form of a solid or a liquid. Additional agents, such as surfactants, may be added to control the release of GHB from within the polymeric bead, such as sodium lauryl sulfate or stearic acid. The beads can be coated with a flexible film. Background information on GHB and its related compounds, use and methods for manufacture are listed below. Also, background information on ion exchange resins, their manufacture and uses can be found in the references listed below. The new formulations of the present invention described herein provide favourable sustained release profiles for GHB.

The following U.S. patents and applications relate to GHB and are hereby incorporated by reference in their entireties for all purposes: U.S. Pat. Nos. 6,472,431, 8,263, 650, 8,324,275; 8,859,619; 7,895,059; 7,797,171; 7,668, 730; 7,765,106; 7,765,107; 8,461,197; 8,591,922; 8,731, 963; 8,759,394; 8,771,735; 8,772,306; 8,778,301; 8,778, 398; 8,901,173; and 2012/0076865. The following patents are also incorporated by reference: U.S. Pat. Nos. 5,380,937; 4,393,236 German Patent DD 237,309 A1; and British Pat. No. 922,029.

Information on ion exchange resins, their manufacture and uses can be found in the following references which are hereby incorporated by reference in their entireties for all purposes. Mahore J. G, Wadher K. J, Umekar M. J, Bhoyar P. K., Ion Exchange Resins: Pharmaceutical Applications And Recent Advancement, International Journal of Pharmaceutical Sciences Review and Research, Volume 1, Issue 2, March-April 2010; Article 002; Munot, Neha M., et al. "Ion exchange resins in pharmaceuticals: A review." Journal of Pharmacy Research 3.12 (2010). Singh, Inderbir, et al. "Ion exchange resins: drug delivery and therapeutic applications." FABAD J. Pharm. Sci 32 (2007): 91-100; Srikanth, M. V., et al. "Ion-exchange resins as controlled drug delivery carriers." Journal of Scientific Research 2.3 (2010): 597; Singh, Inderbir, et al. "Ion exchange resins: drug delivery and therapeutic applications." FABAD J. Pharm. Sci 32 (2007): 91-100; Ohta et al., Development of a simple method for the preparation of a silica gel based controlled delivery system with a high drug content, European Journal of Pharmaceutical Sciences 26 (2005) 87-96; Akifuddin et al., Preparation, Characterization and In-vitro Evaluation of Microcapsules for Controlled Release of Diltiazem Hydrochloride by Ionotropic Gelation Technique, Journal of Applied Pharmaceutical Science Vol. 3 (04), pp. 035-042, April, 2013; Patil et al., A Review On Ionotropic Gelation Method: Novel Approach For Controlled Gastroretentive Gelispheres; International Journal of Pharmacy and Pharmaceutical Sciences, Vol 4, Suppl 4, 2012; Cabellero, et al., Characterization of alginate beads loaded with ibuprofen lysine salt and optimization of the preparation method, International Journal of Pharmaceutics 460 (2014) 181-188; J. M. C. Puguan, X. Yu, H. Kim, Diffusion characteristics of different molecular weight solutes in Ca-Alginate gel beads, Colloids and Surfaces A: Physicochemical and Engineering Aspects (2015), http://dx.doi.org/10.1016/j.colsurfa.2015.01.027; Takka and Gurel, Evaluation of Chitosan/Alginate Beads Using Experimental Design: Formulation and In Vitro Characterization, AAPS PharmSciTech, Vol. 11, No. 1, March 2010; Anand, et al., Ion-exchange resins: carrying drug delivery forward, DDT Vol. 6, No. 17 Sep. 2001. See also the Technical Information sheet for Dowex Ion Exchange Resins; the Product Data Sheet for Amberlite IRN78 Resin, both from Dow Chemicals. Also the Technical Sheet for Duolite AP143/1083 Pharmaceutical Grade Anion Exchange Resin (Cholestyramine Resin USP) from Rohm and Haas. The following U.S. Patents and applications are also incorporated by reference in their entireties for all purposes U.S. Pat. Nos. 4,221,778; 4,510,128; 6,322,819; 8,193,211, 8,202,537; 8,771,735; 8,778,398, 8,062,667, and 8,337,890; U.S. Patent Publication Nos. 2003/0180249; 2008/0003267; 2008/0118571; 2012/0076865; 2012/0148672; 2013/0273159; 2014/0004202; 2014/0093578; and 2014/0127306.

As used herein, the term gamma-hydroxybutyrate (GHB) or "oxybate" refers to the negatively charged or anionic form (conjugate base) of gamma-hydroxybutyric acid. The manufacture, use, known dosage forms and dosing can be shown in the above patents. An effective dosage range of Xyrem is 6 g to 9 g, given at night in divided doses approximately 2-4 hours apart. GHB is typically given twice nightly due to a short in vivo half-life. It is subject to a controlled drug distribution system. See U.S. Pat. Nos. 6,472,431, 8,263,650, 8,324,275; 8,859,619; 7,895,059; 7,797,171; 7,668,730; 7,765,106; 7,765,107; 8,591,922; and 8,772,306 which are incorporated above.

One object of the invention is to maintain the concentration of GHB in the blood at levels sufficient to promote sleep for up to 8, 7, 6, or 5 hours. As described above, a single dose is eliminated within a shorter period of time. One object of the invention is to maintain the blood level of GHB from about 10 mg/L to about 20 mg/L for up to 8, 7, 6, or 5 hours. Additionally, it is an object of the invention to ensure that the sleep inducing effects of GHB do not remain for longer than the above periods as it would compromise a patient's ability to perform normal day to day activities, such as work or driving a car. One embodiment of the invention is a controlled release formulation of GHB designed to maintain a level of GHB in the blood that satisfies the above criteria. In addition to the controlled or extended release properties of one embodiment, there can be an immediate release GHB formulation that is present in or accompanies the controlled release formulation. A sufficient amount of GHB must be present in the blood to initiate the sleep function of GHB and then the controlled release component may engage to maintain the blood concentration above the threshold for a complete sleep of sufficient duration. It has been discovered that administration of food may extend the effects of GHB in some circumstances and care should be taken to consider this effect during administration. See U.S. Pat. Nos. 8,859,619; 8,778,398 and 8,591,922 as well as U.S. Pat. Publication 2012/0076865 among others.

The buffering capacity of GHB may affect gastric pH and compromise performance of enteric-coated dosage forms. Avoidance of the potential impact on gastric pH is another useful feature of the GHB resinate, since it has no effect on gastric pH.

In one embodiment, the present invention is directed to formulations of drugs that are carboxylic acids, as described herein, and are suited to the controlled release of high dose drugs that are highly water soluble. In addition, in certain embodiments, the formulations described herein provide controlled release of drugs that are highly hygroscopic, even where such drugs must be administered at relatively high doses. In particular embodiments, the controlled release formulations are provided as a unit dose or liquid dosage form.

The formulations and dosage forms of the present invention can also include an immediate release component. The immediate release component can form part of a solid controlled release unit dosage form or liquid dosage form (e.g., combined with a controlled release GHB resinate component) or may be a separate immediate release composition. Therefore, an immediate release component may be provided, for example, as a dry powder formulation, an immediate release tablet, an encapsulated formulation, or a liquid solution or suspension. However, the immediate release component may also be formulated as part of a single dosage form that integrates both the above components. The immediate release component can furthermore be an oxybate salt such as sodium, potassium, calcium, or magnesium, the immediate release component can also comprise the GHB resinate particles without modification to retard release, or a combination of these GHB forms.

In specific embodiments, controlled release and immediate release formulations can be dosed together to a subject to provide quick onset of action, followed by maintenance of therapeutic levels of the drug substance over a sustained period of time. However, because the controlled release component and immediate release component described herein need not be present in a single dosage form, as it is used herein, the phrase "dosed together" refers to substantially simultaneous dosing of the controlled release and immediate release components, but not necessarily administration in the same dosage form. Dosing the controlled release and immediate release components together offers increased convenience, allowing patients to quickly achieve and maintain therapeutic levels of a drug over a sustained period of time, while reducing the frequency with which the drug must be dosed. Furthermore, dosing the controlled release and immediate release components together may avoid the disadvantages of dosing regimens and formulations that result in highly pulsatile plasma concentrations.

Gamma butyrolactone (GBL) is a prodrug for GHB. It can be produced by the dehydrogenation of 1, 4 butanediol. GBL can be hydrolyzed under basic conditions (the use of a metal ion hydroxide) to produce GHB. See Arena, C, et al., "Absorption of Sodium γ-Hydroxybutyrate and its Prodrug γ-butyrolactone: relationship between n vitro transport and in vivo absorption", Journal of Pharmaceutical Sciences, 69(3), (March 1980), 356-358; and Lettieri, J, et al., "Improved Pharmacological Activity via Pro-Drug Modification: Comparative Pharmacokinetics of Sodium Y-Hydroxybutyrate and Y-Butyrolactone", Research Communications in Chemical Pathology and Pharmacology, 22(1), (1978), 107-118.

The required dose of GHB, on a molar basis, is unusually high and quite different from most pharmaceutical agents normally considered for drug-resin complexes. A 9 g dose of sodium oxybate is 71 mMol of oxybate, a carboxylic acid. This stands in contrast to a typical moderately potent active pharmaceutical ingredient (API) having a molecular weight of about 400 daltons and a dose of 400 mg, which results in a molar dose of about 1 mMol. Thus, sodium oxybate dosing is about 70-fold higher (on a molar basis) than a more typical drug.

Much of the dose is required in immediate release form for initial therapeutic benefit. However, due to the buffering effect of oxybate (pKa of 4.5), the immediate-release portion of the dose would cause the gastric pH to increase to about 6. This complicates formulation design, as rate-controlling polymers often have pH-dependent dependent solubility. In particular, if delayed release via enteric coating is desired, then upon release of the immediate release portion of the dose, the concomitant rise in gastric pH could result in at least partial dissolution of the enteric coating, thereby compromising the delayed release function of the enteric coating.

The solubility of sodium oxybate is unusually high. For example, a Xyrem solution is provided as 500 mg/mL concentration in water, or 42 wt %, and its solubility limit is considerably higher. Furthermore, due to the small size and ionic nature of GHB at physiological pH, the drug is unusually mobile in solution. Those skilled in the art will appreciate that these factors complicate and, in many cases, limit conventional approaches for modified release, such as core/shell or matrix formulations, as the high solubility and mobility of GHB would tend to significantly reduce the number of viable approaches using such conventional solubility and diffusivity control technologies.

Furthermore, while extended release oxybate dosage forms are known, such extended release dosage forms are provided as solids, e.g. as tablets. Because the required dose of oxybate is high, such tablets can be quite large, and/or require the administration of multiple tablets. This can be problematic because some patient populations have difficulty swallowing solid dosage forms, or the need to swallow multiple tablets may reduce patient compliance. In addition, the sustained release matrix or coating compositions used to provide extended release are complex and expensive to produce. Accordingly, it would be desirable to provide oxybate (or analogous drugs which require administration in high doses) in an extended release, oral liquid dosage form (including suspensions of oxybate-containing particles as described herein, which in some embodiments can be supplied as a sachet which can be suspended in e.g., tap water by the end user), using simply, readily controlled processing methods.

A drug-resin complex may address some of these limitations, as the drug is essentially insoluble as long as it remains bound to the resin. Instead, the drug release is regulated by exchange with other anions present in the gut, the most prevalent being chloride. Thus, the nature of the formulation challenge is to limit the diffusion of chloride anion into the dosage form rather than to limit the egress of the soluble drug, oxybate.

Drug-resin complexes including modified release drug-resin complexes are known. However, such complexes would typically be considered unsuitable for very high dose, low molecular weight drugs such as oxybate, because the molar amount of drug required is quite high, which would therefore necessitate correspondingly large amounts of ion exchange resin, particularly if the efficiency of binding is significantly less than 100%. Accordingly, for drugs such as oxybate that are dosed at much higher molar levels, e.g., approximately 100-fold higher compared to typical drug dosing, drug-resin complexes would not be considered acceptable.

In one embodiment, a particularly convenient means of administering drug resinates is as a suspension of individual drug resinate beads. The beads may be a plurality of individual resin beads, each loaded with drug and optionally coated with a rate-controlling polymer and additives to influence its properties (such as permeability, flexibility, etc.). Coating formulations exist to address processing challenges, such as the swelling of beads and retention of film integrity. One such example is methylphenidate resinate beads as shown in U.S. Pat. No. 8,202,537.

In one embodiment, the present invention provides a GHB formulation which delivers a controlled release profile, for example a controlled release profile suitable for once-a-day dosing as described herein. Due to the prolongation of the drug release, compositions of the present invention are useful because the once-a-day dose provides a more consistent supply (release) of GHB to patients who otherwise may have to take multiple doses a day. In one embodiment, the invention provides a multi-particulate composition, for example a suspension (e.g., homogeneous suspension), or solid compositions such as a tablet, capsule, powder, wafer, or strip system comprised of a plurality of such particles and optionally other excipients.

As used herein, the term "controlled release" refers to compositions, for example GHB resinate compositions as described herein, which are characterized by having at least one of the active components having a release over a period of at least about 2 to about 8 hours, or about 4 to 6 hours, including about 2, about 2.5, about 3, about 3.5, about 4, about 4.5, about 5, about 5.5, about 6, about 6.5, about 7, about 7.5, or about 8 hours, inclusive of all ranges therebetween. The release profile may be assessed using in vitro dissolution assays known to those of skill in the art, e.g., USP apparatus 2 (paddle) or, more preferably, apparatus 4 (flow-through cell). Particularly when the molar dose of oxybate is large and approaches the amount of anion in the dissolution media, a flow-through apparatus is desired so that the media composition and flow rate can better approximate the physiologic state. The release profile can be assessed for example (e.g., for bioavailability determinations), in pharmacokinetic studies using plasma concentrations to assess maximum concentration ($C_{max}$) and area under the curve (AUC). Such assays are well known to those of skill in the art.

In one embodiment, the present invention provides a drug-ion exchange resin composition for further use in a formulation with conventional pharmaceutically acceptable components to provide ingestible compositions. The finished dose compositions may take the form of liquid preparations, such as suspensions, or solid preparations such as tablets, capsules, liquigels, powders, wafers, strips, etc.

Ion-exchange matrices suitable for use in these preparations are water-insoluble and comprise in most embodiments a pharmacologically inert organic and/or inorganic matrix containing functional groups that are ionic or capable of being ionized under the appropriate conditions of pH. In one embodiment, the ion-exchange matrix is anionic. The organic matrix may be synthetic (e.g., polymers or copolymers of acrylic acid, methacrylic acid, sulfonated styrene, sulfonated divinylbenzene, etc.), or partially synthetic (e.g. modified cellulose and dextrans). The inorganic matrix, in various embodiments, can comprise silica gel modified by the addition of ionic groups, or other similar inorganic materials functionalized with ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are examples of materials suitable for use in the controlled release of drug preparations. Such ion-exchangers are described by H. F. Walton in "Principles of Ion Exchange" (pp: 312-343) and "Techniques and Applications of Ion-Exchange Chromatography" (pp: 344-361) in Chromatography. (E. Heftmann, editor), van Nostrand Reinhold Company, New York (1975). A high exchange capacity is desired to limit quantities of resin needed, and that typical values are about 4 mEQ/g In one embodiment, the size of the ion-exchange particles is from about 5 microns to about 1,000 microns. In most embodiments the particle size is within the range of about 50 microns to about 750 microns (including about 50, about 100, about 150, about 200, about 250, about 300, about 350, about 400, about 450, about 500, about 550, about 600, about 650, about 700, or about 740 microns, inclusive of all values and ranges therebetween) for liquid dosage forms, although particles up to about 1,000 micron (including the values and ranges herein, and in addition about 800, about 850, about 900, about 950, or about 1000 microns, inclusive of all values and ranges described herein) can be used for solid dosage forms, e.g., tablets and capsules. Particle sizes substantially below the lower limit are generally difficult to handle in all steps of the processing. Both uncoated and coated drug-ion exchange resin particles may be designed within this size range.

Both regularly and irregularly shaped particles may be used as resins. Regularly shaped particles are those particles that substantially conform to geometric shapes such as spherical, elliptical, cylindrical and the like, (e.g., three dimensional shapes readily described by a three dimensional space group) which are exemplified by (but not limited to) any of the ion exchange resins disclosed herein, for example Dow XYS-40010.00 and Dow XYS-40013.00 (The Dow Chemical Company). Irregularly shaped particles are all particles not considered to be regularly geometrically shaped (for example not readily described by a three dimensional space group), such as particles with amorphous shapes and particles with increased surface areas due to surface channels or distortions. Irregularly shaped ion-exchange resins of this type are exemplified by (but not limited to) any of the ion exchange resins disclosed herein, for example Amberlite IRP-69 (Rohm and Haas). Two of the resins of some of the embodiments of this invention are Amberlite IRP-69 and Dow XYS-40010.00. Both are sulfonated polymers composed of polystyrene cross-linked with about 8% of divinylbenzene, with an ion-exchange capacity of about 4.5 to 5.5 meq/g of dry resin ($H^+$-form). Their essential difference is in physical form. Amberlite IRP-69 consists of irregularly shaped particles with a size range of about 5 microns to about 149 microns produced by milling the parent large size spheres of Amberlite IRP-120. The Dow XYS-40010.00 product consists of spherical particles with a size range of 45 microns to 150 microns.

In one embodiment, suitable ion-exchange resins include anion exchange resins, such as have been described in the art and are commercially available. These resins are particularly well suited for use with acidic drugs including GHB, as well as prodrugs such as GBL, salts, isomers, polymorphs, and solvates thereof, as well as other acidic drugs identified herein and/or known in the art such as salicylates, nicotinic acid, mefanimic acid, methotrexate, furosemide, phenolic drugs such as paracetamol, morphine, and levothyroxine, warfarin, phenylbutazone, indomethacin, barbiturates, phenytoin, sulphonamides, etc.

Any anion exchange suitable for pharmaceutical use can be employed in the compositions of the present invention, particularly strong anion exchange resins. An example of a suitable anion exchange resin is a cholestyramine resin, a strong base type 1 anion exchange resin powder with a polystyrene matrix and quaternary ammonium functional groups. The exchangeable anion is generally chloride which can be exchanged for, or replaced by, virtually any anionic species. Other examples include Type II resins, which contain dialkyl 2-hydroxyethyl ammonium chloride or hydroxide groups. Such Type I and Type II resins are available under the DOWEX® and Amberlite® trade names. A commercially available Cholestyramine resin is PUROLITE™ A430MR resin. As described by its manufacturer, this resin has an average particle size range of less than 150 microns, a pH in the range of 4-6, and an exchange capacity of 1.8-2.2 eq/dry gm. Another pharmaceutical grade cholestyramine resin is available as DUOLITE™ AP143/1094 (Rohm and Haas/Dow), described by the manufacturer as having a particle size in the range of 95%, less than 100 microns and 40%, less than 50 microns. The commercial literature from the suppliers of these and other resin is incorporated herein by reference (PUROLITE A-430 MR; DOW Cholestryramine USP, Form No. 177-01877-204, Dow Chemical Company; DUOLITE AP143/1083, Rohm and Haas Company, IE-566EDS—February 06). Other suitable anion exchange resins include POROS® XQ anion exchange resins available from ThermoFisher Scientific. Both regularly and irregularly shaped particles may be used as resins. Regularly shaped particles are those particles that substantially conform to geometric shapes such as spherical, elliptical, cylindrical and the like, (e.g., three dimensional shapes readily described by a three dimensional space group) Irregularly shaped particles are all particles not considered to be regularly geometrically shaped (for example not readily described by a three dimensional space group), such as particles with amorphous shapes and particles with increased surface areas due to surface channels or distortions. The regular and irregularly shaped particles can comprise any of the anion exchange resins disclosed herein.

For the oxybate resinate compositions of the present invention, the amount of oxybate present in the resinate should be high to minimize the amount of resin required. Furthermore, in most embodiments, the amount of GHB resinate administered, expressed as GHB mEq (i.e., mmoles) is about 20 to about 120 mEq, including about 20, about 25, about 30, about 35, about 40, about 45, about 50, about 55, about 60, about 65, about 70, about 75, about 80, about 85, about 90, about 95, about 100, about 105, about 110, about 115, or about 120 mEq, inclusive of all values and ranges therebetween.

The selected ion-exchange resins may be further treated by the manufacturer or the user to maximize the safety for pharmaceutical use or for improved performance of the compositions. Impurities present in the ion-exchange resins may be removed or neutralized by the use of common chelating agents, anti-oxidants, preservatives such as disodium edetate, sodium bisulfate, and so on by incorporating them at any stage of preparation either before complexation or during complexation or thereafter. These impurities along with their chelating agent to which they have bound may be removed before further treatment of the ion exchange resin with a compound to slow drug release and coating with a diffusion barrier.

Various analogous binding reactions can be carried out for binding an acidic drug to an anion exchange resin. These are (a) resin (Cl⁻ form) plus drug (salt form); (b) resin (Cl⁻ form) plus drug (as free acid); (c) resin (OFF form) plus drug (salt form); (d) resin (OFF form) plus drug (as free acid); (e) resin (OFF form) plus prodrug (γ-butyrolactone). All of these reactions except (d) and (e) have ionic by-products and the anions generated when the reactions occur compete with the anionic drug for binding sites on the resin with the result that reduced levels of drug are bound at equilibrium. For acidic drugs, stoichiometric binding of drug to resin is accomplished only through reactions (d) and (e). The binding may be performed, for example as a batch or column process, as is known in the art.

Typically the drug-ion exchange resin complex thus formed is collected by filtration and washed with appropriate solvents to remove any unbound drug or by-products. The complexes can be air-dried in trays, in a fluid bed dryer, or other suitable dryer, at room temperature or at elevated temperatures which would not degrade the complex.

In one embodiment, the complexes of the present invention can be prepared by batch equilibration, in which a solution of the drug is contacted with finely divided ion-exchange resin powders. While ion exchange resins are typically provided in very fine particle sizes, which render conventional columnar ion-exchange processes inefficient, such methods can be used for ion exchange resins of suitable particle size. The total ion-exchange capacity represents the maximum achievable capacity for exchanging cations or anions measured under ideal laboratory conditions. The actual capacity which will be realized when loading a drug onto ion exchange resin will be influenced by such factors as the inherent selectivity of the ion exchange resin for the drug, the drug's concentration in the loading solution and the concentration of competing ions also present in the loading solution. The rate of loading will be affected by the activity of the drug and its molecular dimensions as well as the extent to which the polymer phase is swollen during loading.

In one embodiment, a batch or equilibrium process is used to load a drug onto an ion-exchange resin. It is usually desirable to load as much as possible of the drug, such as GHB or GBL, onto the ion exchange resin, as typical GHB doses required for treating excessive daytime sleepiness and cataplexy in patients with narcolepsy are quite high. Low loadings of GHB in the resinate would require quite large amounts of resin, resulting in unit dosages which would be too large to be conveniently administered and resin quantities that may give rise to more adverse effects such as gastrointestinal disturbance. Complete transfer of the drug from the loading solution into the ion-exchange resin is not likely in a single equilibrium stage. Accordingly, more than one equilibration may be required in order to achieve the desired loading onto the ion exchange resin. The use of two or more loading stages, separating the resin from the drug-containing liquid phase between stages, is a means of achieving maximum loading of the drug onto the ion exchange resin, although some loss of drug from the liquid phase of the final loading stage may occur.

The efficiency of loading the drug (e.g. GHB) onto the ion exchange resin can be influenced by the counter ion used in the ion exchange resin. Commercially supplied anionic resins for pharmaceutical use are almost exclusively in the chloride form. However, chloride ions have a much higher affinity for the exchange site in the resin relative to GHB. The affinity can be estimated based on the $pK_a$ of GHB (4.44) relative to other short-chain fatty acids for which affinities are known. On that basis, GHB has approximately 18% affinity relative to chloride on the anion exchange resin. Bicarbonate, on the other hand, has an affinity of about 27% affinity relative to chloride. Therefore, when a bicarbonate-exchanged resin is contacted with GHB, a much higher efficiency of GHB incorporation may be achieved, because the affinity of GHB relative to bicarbonate is about 67% vs. about 18% relative to chloride. Other "intermediate" exchange anions can also be used, especially those with low affinity relative to chloride and much lower cost relative to oxybate. Thus in some embodiments, substantially all of the chloride counter ion of the e.g. commercially available pharmaceutical grade anion exchange resin is replaced with the intermediate anion (e.g. bicarbonate), in one or more batch equilibration steps as required. After rinsing with an appropriate solvent, the ion exchange resin exchanged with the lower affinity anion (relative to chloride) can then be then exchanged with oxybate.

Substantially complete incorporation (i.e., expressed as the percentage of theoretically available ion exchange sites) of oxybate in the anion exchange resin is desirable to minimize the amount of anion exchange resin required to provide a specified dose of drug (e.g. oxybate). In practice, 100% incorporation of the drug can be difficult and/or expensive to achieve, so somewhat less than substantially complete levels of incorporation of drug are also suitable. Typically, levels of incorporation of more than about 75% are acceptable, including about 75%, about 80%, about 85%, about 90%, about 92%, about 94%, about 96%, about 98%, about 99%, or about 100%, inclusive of all values and ranges therebetween.

When a multi-step batch equilibration is needed or desirable, the resinate slurry formed during equilibration can be decanted to remove the solution of oxybate. The decant can be collected for potential recovery of oxybate or waste disposal. The resinate is then rinsed with solvent, such as de-ionized water, and then charged to the batch equilibration tank where it is contacted with fresh or recovered oxybate to increase the level of incorporation of oxybate. Multiple equilibration steps can be used with fresh or recycled oxybate solution until the desired level of incorporation, as described herein, is achieved.

Recovery of oxybate from a chloride-exchange process can be very challenging due to oxybate's high water solubility and relatively small size. If aqueous processing is used, all chloride salts are soluble. However, when an intermediate anion (e.g. bicarbonate) is used, the solubility can be manipulated with selection of the cationic form of oxybate. If full and complete exchange of oxybate is desired in one step, then the salt form of oxybate is selected such that the salt form of the exchanged anion is insoluble. For example, calcium salts of many exchangeable anions tend to have very low solubilities. Oxybate can be introduced as calcium oxybate, which is highly water-soluble and suitable for an aqueous exchange process. Precipitation drives the exchange process to near-completion, resulting in very high oxybate yield and incorporation. For example, bicarbonate would precipitate as calcium carbonate if the relatively insoluble calcium hydroxide is added in stoichiometric amount at the commencement of batch equilibration, as shown below. Other example intermediate examples include phosphate (precipitating as calcium phosphate), sulfate (precipitating as calcium sulfate), and hydroxide (precipitating as calcium hydroxide).

$$Ca^{++}(GHB^-)_2 + 2R\text{—}HCO_3 \rightarrow Ca^{++} + 2HCO_3^- + 2R\text{-}GHB; R=\text{resin}$$

$$Ca^{++} + 2HCO_3^- + Ca(OH)_2 \rightarrow CaCO_3(s) + H_2O$$

Use of precipitation as a means to drive batch equilibration can result in some difficulties in recovering the resin, as the resinate and precipitate can both be small particles. In some embodiments, the exchange process is carried out under conditions such that all species remain soluble, and therefore the resinate and solution are easily separated. Next, the oxybate is recovered from the solution in a separate vessel by performing a displacement precipitation by addition of another salt or base. For instance, in the above example, the calcium hydroxide can be added in a separate step, thereby avoiding a difficult separation problem. Although this process may provide a somewhat less efficient equilibration per batch cycle, recovery of the un-exchanged oxybate can be nearly 100%, and multiple batch equilibrations can be performed economically. The technique can be more generally applied if sodium oxybate is used in the exchange process, because most sodium salts of the exchanged anion would remain soluble. In the recovery step, a calcium salt or base is added in near-stoichiometric amount to precipitate the exchanged oxybate and enable full recovery of the sodium oxybate. In one embodiment, calcium hydroxide is added to facilitate recovery. Because it has low solubility, calcium hydroxide can be used in excess without appreciably contaminating the recovered sodium oxybate with calcium.

$$Na^+GHB^- + R\text{-}HCO_3 \rightarrow Na^+ + HCO_3^- + R\text{-}GHB; R=\text{resin}$$

$$2Na^+HCO_3^- + Ca(OH)_2 \rightarrow CaCO_3(s) + 2H_2O$$

In yet another embodiment of processes for forming the GHB resinate, the anion can be recovered by sub-stoichiometric addition of the soluble calcium oxybate to the sodium-exchanged intermediate anion in the recovery process. Most of the sodium oxybate can be recovered and recycled without causing precipitation during the batch equilibration.

In a particular embodiment, bicarbonate can be evolved as $CO_2$ gas and the sodium ions form sodium oxybate by adding GBL. This avoids a potentially difficult separation of precipitate during recovery. The sodium bicarbonate is first converted to sodium carbonate, and then the sodium carbonate is reacted with GBL to yield sodium oxybate and carbon dioxide as shown below.

$$NaOH + NaHCO_3 \rightarrow Na_2CO_3 + H_2O$$

$$2GBL + Na_2CO_3 + H_2O \rightarrow 2Na\text{-}GHB + CO_2(g)$$

In yet another embodiment, the bicarbonate form of an anion exchange resin (e.g., and type 1 strong base anion exchange resin), prepared, for example by ion exchange of the chloride form with sodium or potassium bicarbonate (or other soluble bicarbonate salts), is equilibrated with a solution of sodium or potassium oxybate. The resulting oxybate resinate can be separated from the oxybate equilibration solution by known methods (decanting, filtering, etc.). The oxybate equilibration solution can then be treated with sodium or potassium hydroxide to increase the pH, and then contacted with GBL. At the elevated pH, the GBL reacts with exchanged bicarbonate to form additional GHB (oxybate) and carbon dioxide, thereby regenerating the oxybate equilibration solution so that it can be reused, as the bicarbonate ions produced during the initial ion exchange/equilibration step is lost as carbon dioxide gas. The regenerated oxybate equilibration solution can then be re-equilibrated with the oxybate resinate formed in the initial equilibration step, so as to further increase the degree of exchange of oxybate in the resinate. The regenerated equilibration solution can be further regenerated, and further equilibrated with the oxybate resinate as many times as is needed or desired to obtain the desired degree of incorporation of oxybate in the oxybate resinate. A further advantage of this method is the minimization of oxybate waste due to the ability to regenerate and recycle the oxybate equilibration solution.

High loading capacity will be favored by high charge density in the drug. A high loading rate is favored by lower molecular weight. Higher drug concentrations in the loading solution, with a minimum of competing ions, will also favor higher adsorption capacity.

Thus, in one aspect, the invention provides drug-ion exchange resin complexes comprising a drug loaded in an ion exchange resin as described herein. The drugs and ion exchange resins may be readily selected from amongst those drugs and resins described herein. In most embodiments, GHB and GBL are suitable drugs. The invention further provides drug-ion exchange resin matrixes defined as follows.

The drug-ion exchange resin complexes of the present invention can readily be formulated with pharmaceutically acceptable excipients according to methods well known to those of skill in the art, for example as described in Remington, The Science and Practice of Pharmacy, 22 Edition Philadelphia College of Pharmacy 2013 Pharmaceutical Press, herein incorporated by reference in its entirety for all purposes. In one embodiment, these formulations contain a substantially coated drug-ion exchange resin complex of the invention, optionally with a compound that will slow the release of the drug. In another embodiment, such formulations may also contain a selected amount of uncoated drug-ion exchange resin complex, optionally with a compound to slow the release as described herein. In certain formulations, mixtures of coated drug-ion exchange resin complexes and uncoated drug-ion exchange resin complexes are present. These formulations may contain any suitable ratio of coated to uncoated product.

In one embodiment, the controlled release dosage form includes drug loaded onto beads (e.g., ion-exchange beads) in combination with one or more optional excipients, such as binders, fillers, diluents, disintegrants, colorants, buffering agents, coatings, surfactants, wetting agents, lubricants, glidants, or other suitable excipients. In one embodiment of the compositions of the present invention that can be fashioned into a tablet or other solid form, beads containing GHB or GBL can include one or more binders that are known for use in tablet formulations. In one such embodiment, the solid form may include at least one binder selected from hydroxypropyl cellulose (HPC), ethylcellulose, hydroxypropyl methylcellulose (HPMC), hydroxyethyl cellulose, povidone, copovidone, pregelatinized starch, dextrin, gelatin, maltodextrin, starch, zein, acacia, alginic acid, carbomers (crosslinked polyacrylates), polymethacrylates, carboxymethylcellulose sodium, guar gum, hydrogenated vegetable oil (type 1), methylcellulose, magnesium aluminum silicate, and sodium alginate. In specific embodiments, the solid form included in a controlled release dosage form as disclosed herein may comprise binder levels ranging from approximately 1% to 10% by weight. For example, the CR core may include a binder in an amount selected from about 1%, 1.5%, 2%, 2.5%, 3%, 3.5%, 4%, 4.5%, 5%, 6%, 7%, 8%, 9%, and 10% by weight, including all ranges therebetween. In certain such embodiments, the amount of binder included in the CR core may range from about 1 to 2%, 1 to 3%, 1 to 4%, 1 to 5%, 1 to 6%, 1 to 7%, 1 to 8%, 1 to 9% and 1 to 10% by weight.

One formulation of the present invention may include one or more lubricants to improve desired processing characteristics. One embodiment of the present invention may include one or more lubricants selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate. In another embodiment, one or more lubricants may be added in a range of about 0.5% to 5% by weight. Particular embodiments may comprise a lubricant in a range of about 0.5% to 2% by weight, about 1% to 2% by weight, about 1% to 3% by weight, about 2% to 3% by weight, and about 2% to 4% by weight. In one such embodiment, one or more lubricants may be present in an amount selected from about 0.5%, 1%, 1.5%, 2%, 2.5%, 3%, 3.5%, 4%, 4.5%, and 5% by weight, inclusive of all ranges therebetween. Still lower lubricant levels may be achieved with use of a "puffer" system during tabletting, which applies lubricant directly to the punch and die surfaces rather than throughout the formulation. When "puffer" systems are used for tabletting, the compositions of the present invention can, but need not be, substantially free of lubricant (e.g., include only traces of lubricant deposited by contact with the lubricant coated tablet press).

In certain embodiments, where the compositions of the present invention are provided as liquid compositions, such as suspensions, the compositions of the present invention can further comprise colorants, flavoring agents (natural and articficial), stabilizing agents (EDTA salts, parabens, benzoates), thickeners (tragacanth, xanthan gum, bentonite, starch, acacia, cellulosics), humectants, sweeteners (sucralose, acesulfame K, saccharides, sorbitol, xylitol, mannitol, maltose), etc.

The drug-ion exchange resin composition thus prepared may be stored for future use or promptly formulated with conventional pharmaceutically acceptable carriers to prepare finished ingestible compositions for delivery orally, or via other means. In one embodiment, a tablet of the invention is formulated as an orally disintegrating tablet. Such orally dissolving tablets may disintegrate in the mouth in less than about 60 seconds. See U.S. Patent Publication. 2012/0076865.

In one embodiment, the oral liquid compositions of the present invention may also comprise one or more surfactants in amounts of up to about 5.0% w/v or from about 0.02 to about 3.0% w/v of the total formulation. The surfactants useful in the preparation of the finished compositions of the present invention are generally organic materials which aid in the stabilization and dispersion of the ingredients in aqueous systems for a suitable homogenous composition. In particular embodiments, suitable surfactants are non-ionic surfactants such as poloxamers, polyoxyethylene ethers (BRIJ), alkoxylated fatty acids (MYRJ), polysorbates (TWEENs), macrogol mixtures (Gelucire, Labrasol), and sorbitan esters (SPANs). These are produced in a wide variety of structures and molecular weights.

When present, the surfactant component may comprise from about 0.01 to about 2.0% w/v of the total composition (for example 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% w/v, inclusive of all ranges therebetween) and in particular embodiments will comprise about 0.1% w/v of the total of the composition. One or more additional emulsifiers or surfactants can also be employed in one embodiment of the invention.

The sustained-release profiles of drug can be obtained by using a mix of uncoated and semipermeable coated resinates and by selecting the degree of cross-linking and particle size of the resins without a coating process. Examples of ion exchange resins include simple resinates (i.e., uncoated drug-ion exchange resin complexes), microencapsulated or coated resinates (i.e., coated drug-ion exchange resin complexes), hollow fiber systems (i.e. hollow fibers with drug containing lumen), sigmoidal-release systems. Examples of such drugs are frusemide, cyclosporin, allopurinol and ciprofloxacin. See Mahore et al. Formulation of such drugs as resinates according to the present invention permits particle sizes that make such release characteristics (e.g., sigmoidal) feasible at reasonable coating weights.

Some embodiments of the present invention involve direct synthesis of oxybate resinate from one or more precursors. Using a hydroxide-form Type 1 strong base anion exchange resin, essentially 100% loading efficiency can be achieved with a simple aqueous reaction with GBL.

The ability to prepare an oxybate resinate, at high loading, in a one step process from GBL can be amenable to point-of-use synthesis (either in patient's hands or at clinical site), as it does not involve shipping or handling the regulated API (GHB). Such a direct synthesis can be carried out using a batch or equilibrium process as described herein, wherein a GBL loading solution is contacted with the particulate hydroxide-form strong base anion exchange resin. The GBL reacts in situ to form an ionic complex of oxybate with the ion-exchange resin, and releasing water as a by-product. It is possible to get 100% yield as well as 100% loading efficiency (i.e., oxybate ionically bound to 100% of the available binding sites) on the resin by such processes. For example, loading efficiencies higher than about 65% (e.g., 65, 70, 75, 80, 85, 90, 95, 96, 97, 98, 99, or about 100%, including ranges therebetween, can be achieved). Because GBL is uncharged and the reaction does not produce ionic byproducts, there are no anions to compete for reaction on the site. Such conditions can achieve 100% reaction on the resin, so the hydroxide-form resin can be used safely, whereas in other applications this may not be possible for patient safety reasons because any unexchanged hydroxide would leave the resin as sodium hydroxide, raising the pH at site of delivery and potentially causing gut wall irritation.

The one-step process is also advantageous because it simplifies purification of the GHB resinate. Because the reaction occurs on the resin and not in the bulk solution, any byproducts that would be made are rinsed off the product. These include any of the impurities in the GBL starting material, as well as unreacted GBL.

Because of the unusually large molar amount of GHB in the compositions of the present invention, relative to the molar quantity of anion present in the gut, the present inventors have found that the compositions of the present invention can provide sustained release without the use of diffusion controlling coatings on the resinate particles. The present inventors have recognized that because the volume and anion content of gastric juice in the fasted state is lower than the molar dose of GHB required for treating the conditions described herein, the rate of GHB release is strongly influenced by the rate of physiological production of anions, and therefore suitable GHB release profiles can be provided without the use of diffusion controlling coatings. For example, while the resinate beads are retained in the stomach, the release of GHB from the resinate beads provided by ion exchange with gastric ions (mainly Cl$^-$) can be limited by the rate of stomach acid secretion. Similarly, as the resinate beads transit the duodenum and small intestine, the remaining dose of bound GHB can exceed local anion capacity. Thus, the rate of GHB release can be limited by the rate of secretion or diffusion of anions into the gut.

The basal anion capacity of the GI tract is quite small. As summarized in McConnell (Int J Pharm 2008, 364: 213-226, Table 1), fasted state basal values of bile salts are so low that they may be ignored. The fasted state chloride balances are 4.6 mEq in the stomach and 13.1 mEq in the small intestine. Compared to an oxybate dose of about 100 mEq, there is almost an order of magnitude deficiency in resident anion capacity for exchange. Such a situation would not occur with the vast majority of drugs having doses in the <1 mMol range.

|  | Stomach | Small intestine |
| --- | --- | --- |
| Volume, mL | 45 | 105 |
| Chloride, mM | 102 | 125 |
| Total mEq | 4.6 | 13.1 |

Therefore, the present inventors have discovered that the release of the ion-exchange resin-bound oxybate can be limited by secretions of anions in the GI tract, of which chloride is dominant. In the stomach, basal acid output (as chloride) is about 3 mEq/h in the fasted state. Even in the event that fed-state behavior is induced upon dosing, the fed state maximum secretion is only about 25 mEq/h. Therefore, the stomach cannot support full exchange at rates required to impart a meaningful duration of effect.

Chloride is actively secreted in jejunum, at a rate of about 4 mEq/h/30 cm under conditions where 120 mM chloride is already present. (Davis G R, et al, Active chloride secretion in the normal human jejunum, J Clin Invest 66:1326-1333 (1980)) This translates to a basal rate of about 32 mEq/h in absence of a chloride gradient. In presence of a gradient, the present inventors have found that the contribution of passive diffusion can be be sufficient, but may still provide a meaningful impediment to full and timely release of oxybate from the resin.

In the ileum, chloride secretions are substantially less, as characterized by Turnberg. (Turnberg L A et al, Interrelationships of chloride, bicarbonate, sodium, and hydrogen transport in human ileum, J. Clin Invest, 49: 557-567 (1970)). Most chloride secretion is associated with bicarbonate exchange when levels are high. One skilled in the art would appreciate that the perfusion studies by Turnberg indicate that chloride secretion in the ileum would almost certainly be insufficient to support the required exchange with GHB-resinate. For example, even in the extreme case where bicarbonate is almost 90 mM and chloride is only 40 mM, the chloride secretion—taking into account the whole length of ileum—would be expected to be at most 23 mEq/h. In the more typical case where bicarbonate is 40 mM, chloride is actually absorbed rather than secreted—even when chloride levels are set at 40 mM. Yet ileal fluid is maintained isotonic.

To further add to the limitations of biology, the reservoir of small intestinal fluid is small and not well distributed. Only about 10% of the physical volume of the small intestine is filled with fluid. The fluid is not continuously and evenly distributed, as reported by Schiller (Schiller C, et al, Intestinal fluid volumes and transit of dosage forms as assessed by magnetic resonance imaging, Aliment Pharmacol Ther 2005; 22:971-979) but rather the majority of fluid exists in about 4 fluid pockets that access a relatively small amount of available surface area. This is not very limiting for non-resinate dosage forms, as long as drug dissolution can occur, as once the drug is dissolved, it can access most of the surface area of the small intestine for absorption. A resinate, on the other hand, requires exchange with dissolved anions in order to provide release of the drug. As exchange occurs, oxybate is released to, and chloride is depleted from, the surrounding fluid. Further exchange is limited until oxybate is absorbed and chloride is replenished in the surrounding fluid—both processes that require fluid contact with intestinal surface. Therefore, if only 10% of the intestinal surface is physically available at any given time, the rate of chloride replenishment must be 10-fold higher to reliably compensate. One skilled in the art considering these unusual aspects would conclude that, in the face of insufficient resident anion capacity in the small intestine, a resinate dosage form would not release its drug completely and, furthermore, what release occurs may not be well-regulated.

Given the above observations, permeability and amount of film may require adjustment to achieve the intended release profile.

Optionally, the release of GHB can be tailored by changing the bead size and/or degree of crosslinking of the beads to provide additional resistance to diffusion. For example, larger resinate beads have a lower surface area/volume ratio than smaller resinate beads, and therefore would release GHB more slowly than the smaller beads in the presence of a solution of the same ionic strength. Similarly, the degree of crosslinking of the beads relates to the degree of swelling of the beads, which in turn is related to the rate at which ion exchange, and this drug release can occur. Specifically, more highly crosslinked beads swell less, and thus have slower ion exchange kinetics, compared to less highly crosslinked beads, Thus, the kinetics of drug release can also be controlled by manipulating the degree of crosslinking of the beads. Effects of particle size, particularly 100 microns or greater, and crosslinking, particularly 4% or greater, that may be modest under normal circumstances may be more impactful in the absence of a rate-controlling coating and when gut anion concentrations are substantially diminished.

If no diffusion controlling coating is required, other processing schemes for making the resinate can be considered to improve manufacturing flexibility. For example, instead of using ~100 micron beads, the drug (e.g., GHB or GBL) can be loaded onto larger beads (e.g., 600 micron beads), and then ground to the desired particle size, particle size distribution, consistency, etc. to select or control the desired release characteristics. This could be carried out in an aqueous suspension, so that no isolation or drying of the resinate would be needed. Moreover, if there is no need to coat the particles (e.g., with a diffusion for coating), the irregular shape or dispersity in size distribution of ground particles, which is normally a complicating factor for coating processes, is not an issue.

In other embodiments, the compositions of the present invention can provide differential displacement of drug (e.g. oxybate) from the resinate. Core/shell release characteristics in the resinate beads can be provided by (a) loading oxybate onto an ion exchange resin such that complete loading is achieved, then (b) coating the beads with a portion of lipophilic agent (i.e. lipophilic anion) having much higher selectivity for the ion-exchange resin than GHB. The lipophilic agent will deposit in the outer shell, at the first sites it contacts, and will be relatively immobile resulting in reversible blockage of the bead pores. Suitable lipophilic agents would be, for example, sulfate salts of medium or long-chain fatty acids, such as sodium lauryl sulfate (SLS), or sulfonic esters, such as dioctyl sulfosuccinate (docusate). Other suitable agents may include alkylbenzene sulfonates, 2-naphthalene sulfonate, phenol, salicylic acid, or any other species that may bind more strongly to the resin than oxybate. In particular embodiments, the lipophilic agents are those which are bulky or present hydrophobic tails that may further hinder diffusion of chloride into the resin pore, or oxybate out of the pore after exchange. Although many effective agents may, in other contexts present toxicity concerns, because such agents are strongly bound to the resin, exposure of the agent to the patient is limited. In one embodiment, the lipophilic agent acts as a diffusion barrier both by blocking pores and by facilitating pore blockage by other hydrophobic agents, for example those added during manufacturing, or which may be present in the patient's digestive tract after administration. For example, if sufficient amounts of a surfactant such as SLS is employed, then a non-ionic hydrophobic agent may be more effectively introduced into the bead pore volume due to its compatibility with the hydrophobic "tail" of the SLS molecule. This provides retarded initial release of the drug (e.g., GHB). In other embodiments, further heat treating of the resinate beads can reduce the variability of release, or further retard release. In other embodiments the compositions of the present invention can comprise more than one population of beads, in which one or more of the bead populations is treated with a lipophilic agent, a combination of a lipophilic agent and a hydrophobic agent, or heat treated to as to provide the desired release characteristics. For example, untreated beads would provide more immediate or faster release, and treated beads would provide delayed or slower release.

If further control of release is needed, in a further embodiment the present invention provides a novel method for preparing GHB-containing resinate beads coated with a diffusion rate controlling coating. This embodiment takes advantage of the driving force supplied by reaction of GBL on the active (hydroxide-bearing) sites of hydroxide-form ion exchange resin beads, and the relatively high diffusion characteristics of the small and uncharged GBL molecule. Hydroxide-form ion-exchange resin beads (of any size) can be coated with a flexible film, such as PVAcetate, Eudragit RS, cellulose acetate 398, a mixture of Eudragit RS/RL or Eudragit NE, ethylcellulose, or an enteric such as Eudragit L100, L55 or FS100 with suitable plasticizer. The coated ion-exchange resin beads are then suspended in de-ionized water to equilibrate. GBL is introduced to the suspended beads, which then diffuses through the rate-controlling film, and reacts progressively with the OH-bearing sites within the resin. Sufficient batch equilibration time is provided to ensure complete reaction. The excess GBL is washed off, and the resulting wet resinate beads have a sustained release coating over GHB resinate, which were formed without starting with GHB resinate. This process may be useful for point-of-use preparation, or can improve the utilization of GBL in preparing the product: no GHB or GBL is lost due to processing during coating, as no GBL is present during the coating process.

In one embodiment of the present invention, the present formulation is administered to a patient once nightly. The patient is administered between 4 g and 10 g GHB/day, or 6 g and 9 g/day. Any of the compositions described herein can be used to provide retarded or delayed release of GHB. For example, the GHB resinate beads may be presented in hydrated form as part of an aqueous suspension, or may be provided as dried beads for mixing with water immediately prior to ingestion or to be taken without water (e.g., as a powder, tablet, capsule etc.). As discussed herein, Type 1 strong base anion exchange resins swell in the presence of water, to an extent that depends on the degree of crosslinking and the nature of the anion bound to it. In the dried state, the sustained release resinate beads of the present invention can hydrate more slowly if release-retarding agents are used. As the beads hydrate, the diffusion of physiologically produced anions of the gastrointestinal tract (e.g. mainly chloride) into the beads can accelerate, thus producing a delayed or gradually increasing rate of release of oxybate.

In another embodiment, a water permeable but relatively insoluble coating is employed over the dry resinate beads such that, when the dry beads are suspended in water, water diffuses through the coating to hydrate and swell the resinate beads. The resulting expansion of the beads causes the coating to rupture, and allow release of the GHB. Suitable polymers for preparing such coatings include one or more of cellulosics such as ethyl cellulose, cellulose acetate, cellulose phthalate; polyvinyl acetate, acrylic polymers and copolymers such as those available under the Eudragit® trade name (e.g., Eudragit® NE30D, RL, and RS resins). Such coatings can be plasticized or unplasticized, and coated onto the beads using methods well-known in the art (pan coating, fluidized bed coating, etc.).

As discussed herein, the dose of GHB required for treating excessive daytime sleepiness and cataplexy in patients with narcolepsy is quite high, resulting in the administration not only of relatively large masses of GHB composition, but also water required for administration (particularly when the GHB composition is aqueous). However, since oxybate is administered at night, administering large quantities of water can cause bedwetting. Accordingly, if administered as an aqueous suspension, the highest practical solids loading is desired. The factors which affect the solids loading (volume fraction) of the suspension include the medium used for dilution (water vs. alcohol) and its viscosity, the degree of swelling of the resinate, the sphericity and uniformity of the beads, and surface charge. See Seno and Yamabe, The Rheological Behavior of Suspensions of Ion-Exchange Resin Particles, Bulletin of the Chemical Society of Japan Vol 39, 776-778 (1966), herein incorporated by reference in its entirety for all purposes. In various embodiments, the compositions of the present invention can be administered as suspended resinate particles in a gel, suitable for ingestion by squeezing from a pouch. In other embodiments, the compositions of the present invention can be dosed in two stages: an initial loading dose followed by a chasing dose. Both the loading and chasing dose comprise suspended beads, but the chasing dose is less concentrated. In still other embodiments, the GHB resinate beads can be administered dry, e.g. by having the patient suck the dry beads through a tube or straw. In such embodiments, an added glidant, which is an excipient used in the art to facilitate powder flow by reducing interparticle friction and cohesion, can be used to facilitate administration. They are used in combination with lubricants as they have no ability to reduce die wall friction. Non-limiting examples include fumed silica, talc, and magnesium carbonate.

The oxybate resinate compositions of the present invention can include an immediate release and an extended release component of oxybate. Such compositions can include, for example, a combination of a population of uncoated resinate beads and a population of resinate beads with a diffusion rate controlling coating as described herein; a single resinate bead population that provides immediate release by ion exchange with physiological anions (e.g. chloride), followed by extended release of oxybate controlled by physiological production of e.g. chloride; combinations of populations of resinate beads having different particle sizes and/or crosslinking densities to control release; or any combination of immediate release and extended release resinate beads disclosed herein.

In one embodiment, the compositions of the present invention may be an immediate-release alternative to Xyrem®. Xyrem® has a steep dose-response curve, and inadvertently taking two doses at the same time would have an adverse effect on the patient. If sodium oxybate is instead provided in resinate form for immediate release, as described herein, the capacity of the stomach and small intestine to provide exchangeable anion would limit the consequences of an inadvertent overdose. A 4.5 g dose of Xyrem is 35.7 mEq oxybate. If the stomach has about 5 mEq chloride, then about 30 mEq of additional exchangeable anion must be provided with the resinate formulation of the present invention to ensure complete release of oxybate. This can be achieved by inclusion of exchangeable anion in the formulation, for example glycine or other amino acids, chloride, or in particular citrate. This embodiment would enable rapid release of the oxybate by providing supplementing exchangeable anions in the stomach.

In another embodiment, the supplemental anions are provided by digestion of proteins administered with or as part of the formulation. The resulting amino acids are then available for exchange with the resin and can provide a more convenient means of providing a large amount of supplemental anion.

In yet another embodiment, the supplemental anions are provided by digestion of a triglyceride administered with the formulation. When the triglyceride empties into the small intestine, lipolysis will generate anions available for exchange. In general, triglycerides of short-chain fatty acids (such as triacetin or tributyrin) can provide better oxybate release than medium- or long-chain triglycerides, because the binding affinity of the resulting anions are higher due to their pKa and size. Triglycerides with at least one short-chain fatty acid component are also suitable, particularly pharmaceutically acceptable short-chain triglycerides such as triacetin.

If the resinate particles are film-coated, then supplemental anions can be provided as separate coated particles, such that the supplemental anion is available when needed. The supplemental anion can be selected such that it is not absorbed rapidly yet has an affinity for the resinate that is much higher than that of oxybate. It can be particularly useful to target or enhance release of the supplemental anion in the ileum where chloride secretory deficit may be most pronounced, since absorption of organic acids might be considerably less in that location. Citric acid, glycine, and mesalazine (5-aminosalicylic acid) are examples of suitable supplemental anions. A non-limiting list of other suitable anions (or conjugate acids) includes pharmaceutically acceptable salts selected from the group consisting of chlorides, acetates, lactates, bicarbonates, sulfates, citrates, tartrates, malates, maleates, malonates, glutarates, succinates, fumarates, aspartates, glutamates, and combinations thereof.

These supplemental anions can be coadministered with the oxybate compositions of the present invention, for example within about an hour (before or after) of administering the drug resinate (e.g., oxybate resinate) compositions of the present invention, or simultaneously therewith. The amount of such supplemental anions can range from about 20 to about 200 mmoles, including about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, or about 200 mmoles, inclusive of all values and ranges therebetween. The supplemental anions can themselves be capable of anion exchange directly upon contact with the drug resinate (e.g., exchanging with the oxybate of the oxybate resinate), or can be "pro-anions"—that is, form anions upon biotransformation after administration to the patient. Non-limiting examples of such "pro-anions" are those described herein, such as triglycerides or proteins. The amount of such "pro-anions" suitable for use in treating patients according to the present invention are amounts that produce between about 20 and about 200 mmoles of anions, as described hereinabove.

If sustained release is desired, then extending gastric emptying can somewhat compensate for deficiencies in the jejunum and, particularly, the ileum. Reliably extending gastric emptying in the fasted state is very challenging. Although some investigators have found that administration of resinate particles can result in mucoadhesion, the unusually high molar doses of GHB of the resinate compositions of the present invention, approximately 100 mEq, will effectively cover the entire surface of the stomach many times over. Thus, observations made with conventional resinate formulations would not apply to GHB resinates. Therefore, a more effective means of promoting gastric retention would be administration of the compositions of the present invention with food or caloric liquid.

The oxybate compositions of the present invention, for example oxybate resinate compositions, provide therapeutically effective levels of oxybate over a period of at least about 3 to about 8 hours. In some embodiments, the composition can be considered to comprise a single population of resinate beads, wherein at least a portion of the resinate beads releases the oxybate quickly upon administration (essentially upon contacting physiologically produced anions such as chloride), and a remaining portion of the resinate beads releases oxybate more slowly, either controlled by the physiological rate of production of anions such as chloride, or by modification of the release characteristics of the resinate beads themselves (e.g., by providing a diffusion controlling coating, by control of bead diameter, or crosslinking density, or other method as described herein). If the compositions of the present invention comprise two or more distinct bead populations (distinguished by their oxybate release characteristics), the rapid (or immediate) release population provides therapeutically effective levels of oxybate for up to about 3 hours (including 1 or 2 hours) after administration, and the other population(s) provide therapeutically effective levels of oxybate for about 3 to about 8 hours (including 3, 4, 5, 6, 7, or 8 hours) after administration.

Xyrem for its approved indications is effective at between 6 g and 9 g administered twice nightly in equal amounts about 4 hours apart. A sustained release equivalent may require a matching AUC as compared to 9 g Xyrem. As disclosed in US2012076865, the overall relative bioavailability of an appropriately-timed sustained release would have at most about 75% relative to Xyrem. Therefore, about 12-13 grams of sodium oxybate would be required, or about 100 mMols.

Suitable blood levels of oxybate are at least about 10 mg/L, ranging up to about 70 m/L, maintained over a period of about 5-8 hours as described herein. For example suitable blood levels of oxybate can be about 10, about 15, about 20, about 25, about 30, about 35, about 40, about 45, about 50, about 55, about 60, about 65, or about 70 mg/L, inclusive of all ranges therebetween.

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particularly suitable modes for its practice. However, those of skill in the art should, in light of the present disclosure, appreciate that many changes can be made in the specific embodiments which are disclosed and still obtain a like or similar result without departing from the spirit and scope of the invention.

All documents cited herein, including patents, patent publications, and non-patent publications are herein incorporated by reference in their entirety for all purposes.

EXAMPLES

Example 1

A gel-type Type 1 strong base anion exchange resin, Dowex 1X2 (Dow Chemical), 100-200 mesh was loaded with GHB as follows. Calcium oxybate was loaded onto resin in a batch equilibration by combining 10 mL of 4 M calcium oxybate solution (approximately 490 mg/mL), 31.7 mL of de-ionized water, and 20.27 g of Dowex 1X2 wet resin as chloride form with 2% crosslinking. After mixing for 2 hours, the resin was filtered under mild vacuum using a Buchner funnel. It was then washed with 700 mL of de-ionized water in approximately 100-150 mL aliquots to remove any free oxybate. The wet beads were then dried in a 60° C. oven for 3.5 hours, and finally sized through a 36-mesh screen. The resinate beads were assayed by suspending 1.5 g of resinate in 12.5 g of 1 M calcium chloride and allowing them to equilibrate overnight at room temperature. The solution was analyzed by HPLC, and the measured oxybate released from the beads was 1.09 mEq per gram of dry resinate. The calculated loading efficiency was 1.14 mEq/gram dry resin, or 33% of the theoretical exchange capacity of the resin.

Example 2

GHB resinate beads were prepared by contacting GBL with another Type 1 strong base anion exchange resin (Amberlite IRN78, Dow Chemical) having a median particle size of about 0.63 mm, as the hydroxide form with 8% crosslinking. Batch B1 was prepared with a 2:1 molar ratio of GBL to hydroxide-bearing sites by suspending 26.78 g of wet resin in 41.2 g of de-ionized water. While stirring, 8.28 g of GBL was added, and the reaction was monitored by HPLC analysis of unreacted GBL. The reaction was largely complete after 30 minutes. After 90 minutes, the resin was filtered under mild vacuum, rinsed with de-ionized water to remove unreacted GBL, and then placed in a 60° C. oven overnight to dry.

Batch B2 was prepared by reacting GBL in only 16% molar excess over hydroxide-bearing sites on the same resin. 2.6 g of GBL was added to 20 g of wet resin (as supplied) while stirring by hand with a spatula. About 5.3 g of additional water was added to facilitate blending. After about 1 hour, the mass was placed in the 60° C. oven overnight to complete the reaction, if necessary. The beads were then rinsed with de-ionized water (70 mL), filtered under mild vacuum, and transferred to the 60° C. oven for drying over 3 days.

The two batches were analyzed for oxybate content by first suspending 1.0 g of resinate in 20 mL of 2 M NaCl for 2 hours with stirring. 10 mL of the resulting solution was then titrated with 1 N HCl and the results were compared with a blank of 10 mL of 2 N NaCl. The initial pH values of B1 and B2 were 7.0 and 8.3, respectively, thus indicating that very little, if any, unreacted hydroxide was present in the resinate product. The oxybate titration indicated that GHB loadings of 4.2 and 4.3 mEq/g dry resin for B1 and B2, respectively. The result further indicates that complete reaction occurred, as the theoretical capacity of the resin is approximately 4 mEq/g.

Example 3

A larger batch of GHB resinate beads are prepared by reacting GBL with Amberlite IRN78 under conditions represented by Batch B2. GBL (36.9 g) is slowly added to a slurry of wet resin (Amberlite IRN78, 279 g) and water (about 200 g). The reaction is allowed to proceed for at least 1 hour at room temperature, with stirring. The product is vacuum filtered, then rinsed with several volumes of de-ionized water. The wet product is then placed in a 40° C. oven to dry overnight. 2.1 g of dried GHB resinate beads are then administered to each of 6 beagle dogs, fasted and weighing approximately 10-12 kg, by oral gavage. Blood is sampled at 0.5 h, 1 h, 2 h, 3 h, 4 h, 6 h, 8 h, and 10 h for determination of plasma GHB content.

Example 4

Amberlite IRN78, a hydroxide form Type 1 anion exchange resin, is charged to a vessel and contacted with a 1M solution of sodium oxybate in a 2:1 stoichiometry to resin equivalents. After about 2 hours of equilibration, the mixture of sodium oxybate and sodium hydroxide is filtered from the resulting resinate. A sample of the solution is titrated to determine sodium hydroxide content, and then an equivalent amount of calcium oxybate is charged to the solution to precipitate calcium hydroxide. The calcium hydroxide is filtered from the solution of sodium oxybate, and the recovered sodium oxybate solution is returned to the equilibration tank and contacted with the wet resinate for 2 hours. The resinate is then filtered, and filtrate is recovered. The recovered filtrate is processed with calcium oxybate as in the first step, and set aside for future use. The resinate product is washed with several volumes of de-ionized water, and then dried.

Example 5

Cholestyramine (chloride form) is charged to a vessel and contacted with 1M sodium bicarbonate in a 2:1 stoichiometry (bicarbonate to resin). Five cycles of batch equilibration (2 h each) are conducted. The solutions in each cycle are not recycled, and resinate is rinsed with 2 volumes of de-ionized water between each cycle.

The wet, bicarbonate-exchanged resin is then contacted with 1M sodium oxybate in a single equilibration step in a 2:1 molar ratio of oxybate to resin. After 2 h, the resinate is filtered, and filtrate collected. Separately, the GHB-resinate is then washed with several volumes of de-ionized water. A sample of the first filtrate is titrated for bicarbonate content, and then a stoichiometric amount of calcium oxybate is added to the batch filtrate. The precipitated calcium carbonate is removed by filtration of the suspension, and the sodium oxybate solution is recovered and stored for future use.

Example 6

The above examples can involve difficult separation steps, as precipitated calcium carbonate is a thick slurry of fine particles at the concentrations used. In this example, filtration is avoided by use of a reaction in which the byproduct forms carbon dioxide rather than a precipitate.

The wet, bicarbonate-exchanged resin of Example 5 is contacted with 1M sodium oxybate in a single equilibration step in a 2:1 molar ratio of oxybate to resin. After 2 h, the resinate is filtered, and filtrate collected. Oxybate is recovered and bicarbonate is removed from the filtrate by addition of a stoichiometric amount of sodium hydroxide such that the bicarbonate is converted to carbonate by the reaction: $NaOH+NaHCO_3 \rightarrow Na_2CO_3+H_2O$. The pH drives this reaction to completion.

Next, GBL is added at a 1:1 stoichiometry. Sodium carbonate reacts with the GBL with the evolution of carbon dioxide gas, which drives the reaction to completion: $2\ GBL+Na_2CO_3+H_2O \rightarrow 2\ Na\text{-}GHB+CO_2(g)$. Optionally, a small excess of sodium hydroxide can be added to avoid conversion to bicarbonate during the reaction. This overall process avoids the filtration of carbonate, recovers all the sodium as unexchanged sodium oxybate, and replaces the exchanged sodium oxybate with new oxybate derived from GBL.

Example 7

Soy protein isolate is compressed into oblong or oval tablets of approximately 1000 mg, using compression aids such as fillers, microcrystalline cellulose, and lubricants as required. The tablets are enteric coated separately with two different polymers to achieve dissolution and release of the soy protein isolate in the jejunum and ileum. One batch is coated with Eudragit L30D-55 (jejunum-targeted), and the other is coated with Eudragit L100 (ileum-targeted). At least two of each kind of tablets are taken with one dose of GHB-resinate (35.7 mEq of resinate equivalent to 4.5 g oxybate) in a glass of water. This provides at least 36 mEq of amino acid content, as the protein is hydrolyzed. By releasing the protein in the small intestine rather than stomach, complete and rapid digestion is avoided. Instead, the protein is digested to amino acids more gradually as it transits the small intestine and as the tablet disintegrates. The amino acids are therefore available to facilitate exchange of the GHB-resinate taken concomitantly.

We claim:

1. A pharmaceutical composition comprising a plurality of particles, each comprising oxybate ionically bound to an ion exchange matrix, wherein said composition provides therapeutically effective levels of oxybate for about 2-8 hours after administration of a single dose to a patient in need thereof, and wherein the amount of oxybate in said composition ranges from about 40 mEq to about 100 mEq.

2. The composition of claim 1, wherein the matrix is an anion-exchange resin.

3. The composition of claim 1, wherein oxybate is bound to at least about 65% of the ion exchange sites of the ion exchange matrix.

4. The composition of claim 1, wherein oxybate is bound to at least about 90% of the ion exchange sites of the ion exchange matrix.

5. The composition of claim 2, prepared by reacting a solution of GBL with a hydroxide form of the anion exchange resin.

6. The composition of claim 1, wherein at least a portion of the particles further comprise a diffusion controlling coating.

7. The composition of claim 1, wherein at least a portion of the particles further comprise a lipophilic agent.

8. The composition of claim 7, wherein the portion of particles treated with the lipophilic agent are further treated with a hydrophobic agent.

9. The composition of claim 1, further comprising a first and a second population of particles, wherein each of the first and second populations of particles comprise oxybate ionically bound to an ion exchange matrix, and wherein the first population of particles provides therapeutically effective levels of oxybate for up to 3 hours, and the second population provides therapeutically effective levels of oxybate for an additional 2 to 5 hours.

10. The composition of claim 1, further comprising (a) a pro-anion compound selected from the group consisting of one or more proteins and triglycerides; or (b) a supplemental anion compound.

11. The composition of claim 10, in the form of a unit dose, wherein the amount of oxybate ranges from about 80 mEq to about 100 mEq, and the amount of anions provided by the anion compound before or after biotransformation ranges from about 40 mmoles to about 200 mmoles.

12. The composition of claim 1, wherein the amount of oxybate in said composition is about 100 mEq.

13. A method of preparing the composition of claim 1, comprising reacting GBL with an anion exchange resin.

14. The method of claim 13, wherein:
   (a) a solution of sodium or potassium oxybate is contacted with a bicarbonate form anion exchange resin, thereby forming an oxybate resinate;
   (b) separating the sodium or potassium oxybate solution from the oxybate resinate;
   (c) treating the separated sodium or potassium oxybate solution from (b) with sodium or potassium hydroxide;
   (d) contacting the treated solution of (c) with GBL, thereby forming carbon dioxide and sodium or potassium oxybate.

15. The method of claim 14, wherein the sodium or potassium oxybate solution formed in (d) is recycled and contacted with the separated oxybate resinate of step (b), whereby the amount of oxybate in the oxybate resinate is increased, and steps (b)-(d) are repeated in cycles until the amount of oxybate in the oxybate resinate is at least about 90% of the theoretical amount.

16. A method of treating a disease or condition treatable with oxybate, comprising administering the composition of claim 1 to a patient in need of treatment with oxybate.

17. The method of claim 16, wherein the disease or condition comprises cataplexy or excessive daytime sleepiness associated with narcolepsy.

18. The method of claim 16, wherein whereby the amount of oxybate administered ranges from about 40 mEq to about 100 mEq of oxybate.

19. The method of claim 18, wherein said oxybate is coadministered with a supplemental anion, wherein the amount of supplemental anion ranges from about 40 to about 200 mmoles.

20. The method of claim 18, wherein said oxybate is coadministered with a quantity of protein providing an amount of amino acid after administration ranging from about 40 to about 200 mmoles.

21. The method of claim 16, wherein said composition is in the form of an oral liquid or solid.

\* \* \* \* \*